(12) United States Patent
Burton

(10) Patent No.: US 6,903,243 B1
(45) Date of Patent: Jun. 7, 2005

(54) MULTI-LAYER ABSORBENT WOUND DRESSING

(75) Inventor: Scott A. Burton, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/657,486

(22) Filed: Sep. 8, 2000

(51) Int. Cl.[7] .............................................. A61F 13/00
(52) U.S. Cl. ............................ 602/41; 602/42; 602/56; 604/304; 604/307; 604/378
(58) Field of Search .............................. 602/41, 56, 42, 602/43, 47; 604/304, 307–308, 378, 381, 385.101, 385.08; 424/443, 445

(56) References Cited

U.S. PATENT DOCUMENTS

| | | | |
|---|---|---|---|
| RE24,906 E | | 12/1960 | Ulrich |
| 3,121,021 A | | 2/1964 | Copeland |
| 3,339,549 A | | 9/1967 | Morse |
| 3,389,827 A | | 6/1968 | Abere et al. |
| 3,419,006 A | | 12/1968 | King |
| 3,595,235 A | * | 7/1971 | Jaspersen .................... 604/364 |
| 4,112,213 A | | 9/1978 | Waldman |

(Continued)

FOREIGN PATENT DOCUMENTS

| | | |
|---|---|---|
| CN | 347318 | 12/1998 |
| EP | 0 107 376 A1 | 5/1984 |
| EP | 0 296 787 B1 | 10/1992 |
| EP | 0 997 539 A2 | 5/2000 |
| WO | WO96/13282 | 5/1996 |
| WO | WO 97/06190 | 2/1997 |
| WO | WO97/18890 A1 | 5/1997 |
| WO | WO97/19116 A1 | 5/1997 |
| WO | WO 97/42917 | 11/1997 |
| WO | WO98/09666 | 3/1998 |
| WO | WO 98/31402 | 7/1998 |
| WO | WO 99/13865 | 3/1999 |
| WO | WO 99/13866 | 3/1999 |
| WO | WO99/32272 A1 | 7/1999 |
| WO | WO01/60296 A1 | 8/2001 |

Primary Examiner—Vincent Millin
(74) Attorney, Agent, or Firm—Nancy M. Lambert

(57) ABSTRACT

A multi-layer wound dressing comprising at least two absorbent layers, and materials for forming absorbent layers are provided. The absorbent layers have different absorbencies, with the layer closest to the wound having a lower absorbency than the layer furthest from the wound. The wound dressing typically contains additional non-absorbing layers, such as a backing film and wound-facing film. The dressing provides absorbency of wound exudates while preventing the absorbent material from entering the wound. In specific implementations the dressing is substantially transparent prior to application to a wound, as well as after application to the wound when body fluids have been absorbed.

34 Claims, 1 Drawing Sheet

U.S. PATENT DOCUMENTS

| | | | |
|---|---|---|---|
| 4,146,027 A | * | 3/1979 | Hoey |
| 4,181,752 A | | 1/1980 | Martens et al. |
| 4,310,509 A | | 1/1982 | Berglund et al. |
| 4,323,557 A | | 4/1982 | Rosso et al. |
| 4,324,246 A | | 4/1982 | Mullane et al. |
| 4,499,896 A | | 2/1985 | Heinecke |
| 4,541,426 A | | 9/1985 | Webster |
| 4,595,001 A | | 6/1986 | Potter et al. |
| 4,598,004 A | | 7/1986 | Heinecke |
| 4,667,665 A | | 5/1987 | Blanco et al. |
| 4,684,558 A | | 8/1987 | Keusch et al. |
| 4,737,410 A | | 4/1988 | Kantner |
| 4,755,413 A | | 7/1988 | Morris |
| 4,784,653 A | | 11/1988 | Bolton et al. |
| 4,798,201 A | | 1/1989 | Rawlings et al. |
| 4,860,737 A | | 8/1989 | Lang et al. |
| 4,867,150 A | * | 9/1989 | Gilbert |
| 4,904,247 A | * | 2/1990 | Therriault |
| 4,909,244 A | | 3/1990 | Quarfoot et al. |
| 4,935,087 A | | 6/1990 | Gilman |
| 4,979,946 A | | 12/1990 | Gilman |
| 5,059,424 A | | 10/1991 | Cartmell et al. |
| 5,147,698 A | * | 9/1992 | Cole |
| 5,270,111 A | * | 12/1993 | D'Haese |
| 5,429,590 A | | 7/1995 | Saito et al. |
| 5,445,604 A | | 8/1995 | Lang |
| 5,531,855 A | | 7/1996 | Heinecke et al. |
| 5,591,820 A | | 1/1997 | Kydonieus et al. |
| 5,614,310 A | | 3/1997 | Delgado et al. |
| 5,643,187 A | | 7/1997 | Naestoft et al. |
| 5,674,346 A | | 10/1997 | Kundel |
| 5,733,570 A | | 3/1998 | Chen et al. |
| 5,738,642 A | | 4/1998 | Heinecke et al. |
| 5,837,789 A | | 11/1998 | Stockhausen et al. |
| 5,849,325 A | | 12/1998 | Heinecke et al. |
| 5,941,840 A | | 8/1999 | Court et al. |
| 5,981,822 A | | 11/1999 | Addison |
| 6,060,557 A | * | 5/2000 | Dahmen et al. |
| 6,143,821 A | | 11/2000 | Houben |
| 6,171,985 B1 | | 1/2001 | Joseph et al. |
| 6,198,016 B1 | | 3/2001 | Lucast et al. |

* cited by examiner

MULTI-LAYER ABSORBENT WOUND DRESSING

FIELD OF THE INVENTION

The present invention is directed to novel body fluid absorbing materials; and to absorbent articles used as wound dressings, including multi-layer absorbent articles having at least two absorbent layers.

BACKGROUND OF THE INVENTION

Proper wound dressings are an essential medical supply for treating injuries. Without dressings, the wound exudate accumulates and creates breeding grounds for harmful microorganisms. Each year, sterile wound dressings are applied to millions of wounds in order to absorb wound exudate while promoting sterility.

Traditional wound dressings have included various cloth and fiber materials as exudates absorbents, such as cotton pads. Unfortunately, these traditional dressings provide relatively limited absorbency and must be changed frequently. Their ability to preserve sterility is also limited, and scabs that form as the wounds heal tend to stick to the dressings. After the dressings are removed, these scabs are also removed, which can be painful and interfere with healing.

Efforts have been made to improve upon these traditional wound dressings by applying a non-stick perforated film to the wound-facing side of the dressing. These non-stick films are designed to allow wound exudate to penetrate to the absorbent, while restricting the physical contact between the absorbent and wound in an effort to reduce undesirable adherence between the two. However, these perforated films do nothing to improve on the absorbency of traditional absorbent materials used in dressings.

In order to improve upon absorbency, various alternative absorbent materials have been developed. For example, hydrophilic hydrocolloids and hydrogels have been created that provide a translucent or transparent absorbent layer. Such dressings can allow for general inspection of the healing wound. Unfortunately, some such dressings have the problem that the absorbent deforms and partially disintegrates upon swelling. Specifically, as the absorbent takes in fluid, it often bends and buckles such that some of the absorbent material breaks away from the dressing and enters the wound. This absorbent material can be left in the wound upon removal of the dressing, which is undesirable for cosmetic and therapeutic reasons. In addition, such materials often have relatively high moisture content prior to application, which can limit their ability to absorb additional water after they are applied.

Therefore, a need exists for a wound dressing that improves on existing dressing materials and technology.

SUMMARY OF THE INVENTION

The present invention is directed to multi-layer wound dressings. The multi-layer wound dressings allow for high absorbency of body fluids while providing good durability and minimal degradation during use. In addition, in specific implementations, the multi-layer wound dressings are transparent and remain transparent when wet; and the dressings can be cut by clinicians to conform to the shape and size of the wound being covered. Also described are novel compositions useful as body fluid absorbing materials.

The wound dressings of the invention include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the reaction product of a hydrophilic, ethylenically unsaturated monomer. In one implementation, the first absorbent layer includes the reaction product of a hydrophilic, ethylenically unsaturated monomer; an acrylic acid ester of a non-tertiary alcohol having 4 to 14 carbon atoms; and a polar, ethylenically unsaturated monomer. Specifically, the first absorbent layer can contain the reaction product of about 50 to 80 parts by weight of the hydrophilic, ethylenically unsaturated monomer; about 5 to 30 parts by weight of the acrylic acid ester of the non-tertiary alcohol having from 4 to 14 carbon atoms; and about 10 to 40 parts by weight of the polar, ethylenically unsaturated monomer. The polar, ethylenically unsaturated monomer comprises N-vinyl acetamide or partially neutralized acrylic acid in specific implementations. Unless otherwise noted, it is assumed for invention compositions (including absorbent layers and body fluid absorbing materials) comprising the reaction product of various parts by weight of specific monomers that the total monomer composition is 100 parts.

The second absorbent layer is typically positioned in contact with the first absorbent layer and is typically less absorbent of body fluids than the first absorbent layer. The second absorbent layer can also contain the reaction product of an acrylic acid ester of a non-tertiary alcohol having from 4 to 14 carbon atoms; a hydrophilic, ethylenically unsaturated monomer; and a polar, ethylenically unsaturated monomer. In particular implementations, the second absorbent layer contains the reaction product of about 45 to 80 parts by weight of the acrylic acid ester of a non-tertiary alcohol having from 4 to 14 carbon atoms; about 25 to 40 parts by weight of the hydrophilic, ethylenically unsaturated monomer; and about 2 to 20 parts by weight of the polar, ethylenically unsaturated monomer.

The first and second layers are usually formed such that they are in contact with one another across a large surface area. In particular implementations, the absorbent layers are formed by a simultaneous polymerization reaction. In such implementations, the unpolymerized monomer can be deposited simultaneously or sequentially and then cured together. Such simultaneously cured absorbent materials often show enhanced physical integrity because they form a strong interface. It is believed that such strength may be a result of some slight interfacial mixing of the layers prior to and during curing.

The second absorbent layer functions as a "barrier" between the first absorbent layer (which may partially "disintegrate" when exudate is absorbed under some conditions) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins to other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 400 percent of its weight after immersion in an isotonic saline solution after 24 hours at room temperature. The second absorbent layer normally has an absorbency of at least about 50 percent by weight of isotonic saline solution after 24 hours. Unless otherwise stated, the term "absorbency" in the present application refers to the percent by weight of isotonic saline solution absorbed by a material tested according to the Saline Absorbency Method described herein.

Additional layers, such as backing layers, wound-facing layers, and adhesives are also suitable for use in certain implementations of the invention. The invention is also directed to methods of making multi-layer wound dressings, including multi-layer wound dressings in which two or more layers of absorbent are simultaneously cured. Although dressings of the invention can include various materials, the invention is also directed to specific absorbent compositions for use in wound dressings. These compositions include materials containing the reaction product of partially neutralized ethylenically unsaturated carboxylic acids and materials containing the reaction product of N-vinyl acetamide.

The above summary of the present invention is not intended to describe each disclosed embodiment of the present invention, but rather that is the purpose of the following disclosure and claims in addition to the summary.

BRIEF DESCRIPTION OF THE FIGURES

Other aspects and advantages of the invention will become apparent upon reading the following detailed description and upon reference to the drawings in which.

Figure 1A:
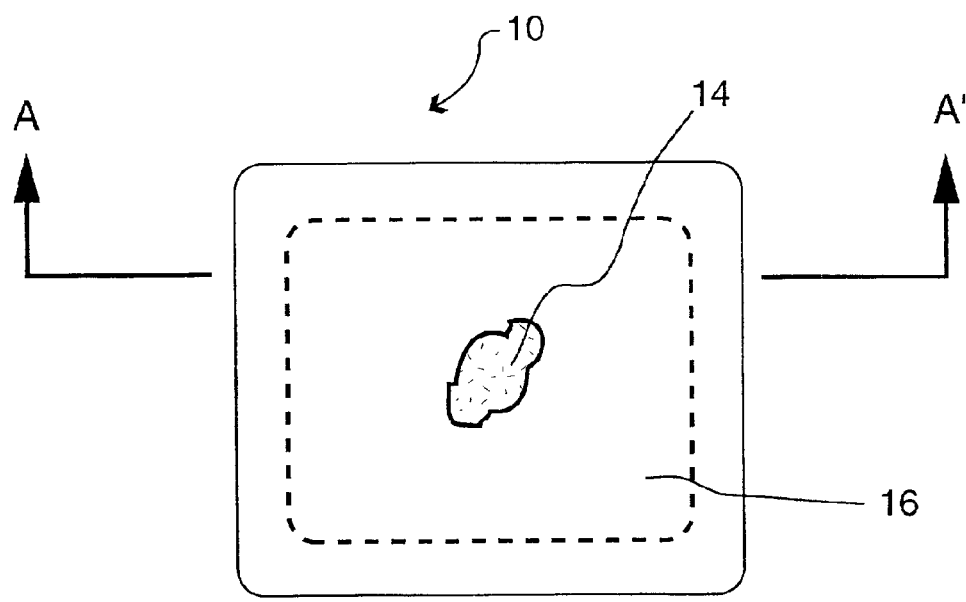
FIG. 1A is a top view of a first wound dressing constructed in accordance with the present invention.

While the invention is susceptible to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The present invention is directed to multi-layer wound dressings that allow for high absorbency of wound exudate. The wound dressings contain absorbent layers that demonstrate low disintegration after absorbing body fluids such that absorbent material does not significantly enter the wound. In addition, in specific implementations, the wound dressings are substantially transparent before and after placement on a wound (with the exception of colored exudate, such as blood), and are formed such that they can be cut to custom sizes by clinicians prior to placement on a wound.

In reference now to FIG. 1A, a top view is shown of a wound dressing 10 constructed in accordance with a first implementation of the invention. Wound dressing 10 is shown adhered on the surface of a patient. Dressing 10 is substantially transparent, with a portion of the wound 14 visible through the top surface 16 of dressing 10. As used herein, transparency refers to dressings that permit viewing of material through the dressing with sufficient clarity to perform general visual examinations. Preferably, the dressings are substantially transparent when the dressings are dry or wet with water or wound exudate. Such transparency typically shows some optical distortion and may include loss in detail and resolution. Also, to the extent the wound exudate is colored by blood or other fluids, the transparency of the dressing is reduced.

Figure 1B:
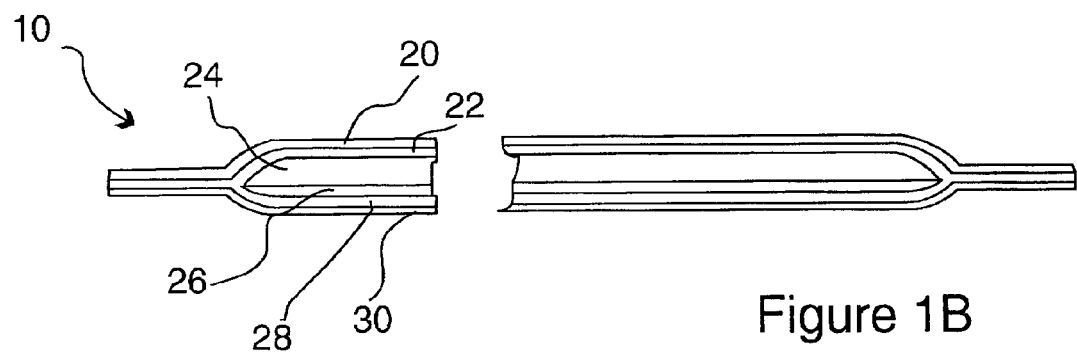
FIG. 1B is a partial cross-sectional view taken along plane A-A' of the wound dressing from FIG. 1A.

A more detailed representation of this example embodiment is shown in FIG. 1B, which is a partial cross section of the wound dressing 10 taken along plane A-A' of FIG. 1A. Wound dressing 10 includes six layers: A backing layer 20, an adhesive layer 22, a first absorbent layer 24, a second absorbent layer 26, a porous or non-continuous wound-facing layer 28; and a pressure sensitive adhesive 30. In the implementation shown, the first and second absorbent layers 24, 26 are positioned only within the interior of dressing 10, while the other four layers extend along the entire dressing 10, and thereby form a perimeter of substantially non-absorbent material. This perimeter can be advantageous because it provides a border and frame for the absorbent layers.

Figure 1C:
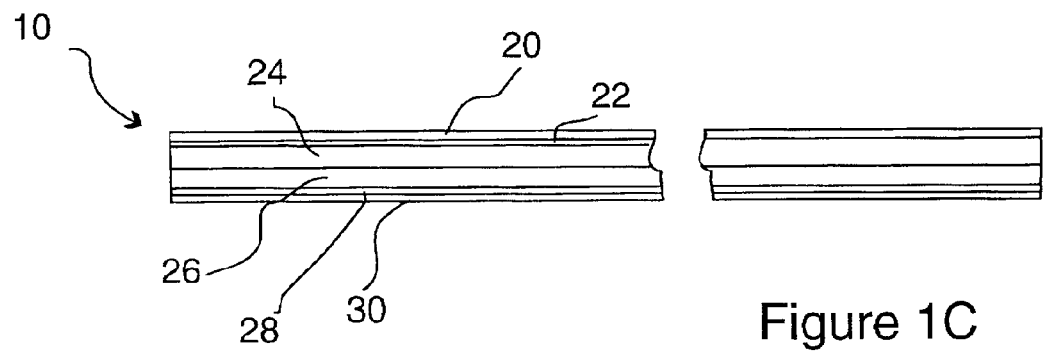
FIG. 1C is a partial cross-sectional view of a second wound dressing constructed in accordance with the present invention.

In other implementations, such as that shown in FIG. 1C, the multiple layers of the dressing 10 extend to the edges of the dressing and thus provide a dressing that can conveniently be cut to size. In the dressing 10 shown in FIG. 1C, the second absorbent layer 26 is substantially adhesive and provides a bond between the first absorbent layer 24 and the wound-facing layer 28. Thus, the multiple layers of wound dressing 10 are held together independent of any edge or frame bonds. This type of wound dressing is particularly well suited to being cut by a clinician to conform to a custom shape because the wound dressing does not delaminate, or delaminates only an acceptable amount, upon exposure to wound exudate. These multi-layer wound dressings show favorable absorption of exudate from wounds while also providing an integrated dressing that avoids significant shedding of the absorbent layers into the wound dressing.

The two implementations shown in FIGS. 1A to 1C depict a six-layer wound dressing, but it will be appreciated that additional layers can be incorporated. In addition, in specific implementations, fewer layers can be used. Thus, the invention is not limited to the embodiments depicted, but rather such embodiments are shown only to illustrate examples of the invention.

The specific materials and positions of the various layers in the wound dressings of the invention will now be described in detail.

A. Absorbent Layers

The present invention features a first absorbent layer comprised of an absorbent composition that is capable of rapidly absorbing moderate to heavy amounts of body fluids, while retaining sufficient structural integrity and transparency. This first absorbent layer typically is the most absorbent material of the dressing. The composition of the first absorbent layer typically includes the reaction product of:

(a) 0 to 30 parts by weight of an acrylic or methacrylic acid ester of a non-tertiary alcohol having from 4 to 14 carbon atoms;

(b) 30 to 100 parts by weight of a hydrophilic, ethylenically unsaturated monomer (more preferably 50 to 80 parts by weight); and (c) 0 to 40 parts by weight of a polar, ethylenically unsaturated monomer different from the hydrophilic, ethylenically unsaturated monomer.

Although various acrylic and methacrylic acid esters of non-tertiary alcohols having 4 to 14 carbon atoms can be used, alcohols having greater than 4 carbon atoms are preferred, and alcohols with from 8 to 12 carbon atoms are particularly preferred.

Examples of suitable acrylic and methacrylic acid ester monomers include esters prepared by reaction with alcohols, such as 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctanol, 2-ethyl-1-hexanol, 1-decanol, 1-dodecanol, 1-tridecanol, 1-tetradecanol, nopol, and the like, as well as combinations thereof. In specific embodiments, the acrylic or methacrylic acid ester is selected from the group consisting of isooctyl acrylate, 2-ethyl hexyl acrylate, isodecyl acrylate, lauryl acrylate, nopol acrylate, and combinations thereof. The amount of the acrylic or methacrylic acid ester typically is less than 80 parts by weight, preferably less than 50 parts by weight, more preferably 5 to 30 parts by weight, and most preferably 10 to 25 parts by weight.

Examples of suitable hydrophilic, ethylenically unsaturated monomers include free radically reactive hydrophilic oligomers (a polymer having a low number of repeating units, generally 2 to 20) and/or polymers including poly(alkylene oxides) (e.g., poly(ethylene oxide)), poly(vinyl methyl ether), poly(vinyl alcohol), cellulose derivatives, and mixtures thereof. Other suitable hydrophilic, ethylenically unsaturated monomers include macromonomers, e.g., acrylate-terminated poly(ethylene oxide), methoxy poly(ethylene oxide) acrylate, butoxy poly(ethylene oxide) acrylate, p-vinyl benzyl-terminated poly(ethylene oxide), acrylate-terminated poly(ethylene glycol), methacrylate-terminated poly(ethylene glycol), methoxy poly(ethylene glycol) methacrylate, butoxy poly(ethylene glycol) methacrylate, p-vinyl benzyl-terminated poly(ethylene glycol), poly(ethylene oxide) diacrylate, poly(ethylene oxide) dimethacrylate, and combinations thereof.

The hydrophilic, ethylenically unsaturated monomer can be acrylate and methacrylate esters prepared from mono-hydroxyl-terminated poly(lower alkylene oxides) such as polyethylene and polypropylene glycols commercially available under the trade designation Carbowax from Union Carbide Corp. in a variety of molecular weights (e.g., Carbowax 350, Carbowax 550, Carbowax 750, Carbowax 2000, and Carbowax 5000). An example of a preferred acrylate-terminated polyethylene glycol is commercially available from Shin-Nakamura Chemical Co., Ltd., Japan, under the designation "NK Ester AM-90G." The hydrophilic, ethylenically unsaturated monomer preferably is selected from the group consisting of acrylate-terminated poly(alkylene oxides) and methacrylate-terminated poly(alkylene oxides). A preferred monomer is an acrylate-terminated methoxy poly(ethylene glycol) monomer. The amount of the hydrophilic, ethylenically unsaturated monomer typically is between 30 and 100 parts by weight, and more typically 50 to 80 parts by weight.

The polar, ethylenically unsaturated monomer preferably is selected from the group consisting of partially neutralized acrylic acid, methacrylic acid, itaconic acid, N-vinyl acetamide, N-methyl-N-vinyl acetamide, N-vinyl propionamide, trialkylaminoethyl(meth)acrylate salt such as trimethylaminoethyl acrylate chloride, N-vinyl-pyrrolidone, N-vinylcaprolactam, hydroxyethyl (meth)acrylate or N-(acryloyloxyethyl)pyrrolidinone; with partially neutralized acrylic acid and N-vinyl acetamide being preferred. The amount of the polar, ethylenically unsaturated monomer preferably is between 0 and 40 parts by weight, more preferably 10 to 30 parts by weight, and most preferably 15 to 25 parts by weight. An example of a preferred absorbent composition is one that includes the reaction product of lauryl acrylate, acrylate-terminated methoxy poly(ethylene glycol), and partially neutralized acrylic acid or N-vinyl acetamide.

The composition used to form the first absorbent layer preferably is tacky after curing and capable of absorbing at least about 200%, more preferably at least about 400%, and most preferably at least about 600% by weight isotonic saline after 24 hours while substantially retaining its structural integrity and transparency. Thus, the first absorbent layer is highly absorbent.

Acrylic acid, methacrylic acid, and itaconic acid contain carboxylic acid group(s), which can react with a base such as sodium hydroxide. For example when one mole of acrylic acid reacts with one mole of sodium hydroxide, one mole of sodium acrylate and one mole of water is produced. In this case, the acrylic acid is neutralized or fully neutralized. A mole of acrylic acid is partially neutralized when it reacts with less than one mole of sodium hydroxide. In general an acid is partially neutralized when one equivalent of acid reacts with less than an equivalent of base. When a ethylenically unsaturated carboxylic acid containing monomer is used in a composition of this invention, it is typically partially neutralized from 1 to 49%. Preferably, the carboxylic acid containing monomer composition is 17% partially neutralized. Neutralization above 49% does not typically produce a clear monomer solution without the addition of a large amount of water.

The second absorbent layer is also typically absorbent, but less absorbent than the first layer. The second layer may contain the same components as described above for the first absorbent layer, however it preferably consists of a higher concentration of the acrylic or methacrylic acid ester monomer and is more tacky. The composition preferably includes the reaction product of:

(a) 45 to 75 parts by weight of an acrylic or methacrylic acid ester of a non-tertiary alcohol having between 4 and 14 carbon atoms, inclusive;

(b) 25 to 40 parts by weight of a hydrophilic, ethylenically unsaturated monomer; and (c) 2 to 20 parts by weight of a polar, ethylenically unsaturated monomer different from the hydrophilic, ethylenically unsaturated monomer, such as partially neutralized carboxylic acid containing monomer; trialkylaminoethyl (meth)acrylates such as trimethylaminoethyl acrylate chloride; N-vinyl amides such as N-vinyl acetamide, N-methyl-N-vinyl acetamide, and N-vinyl propionamide; N-vinyl lactams such as N-vinyl pyrolidinone and N-vinylcaprolactam, hydroxyethyl acrylate, hydroxyethyl methacrylate, or N-acryloyloxyethyl)pyrrolidinone; or combinations of these.

In specific implementations, the composition of the second absorbent layer comprises 55 to 70 parts by weight of an acrylic or methacrylic acid ester of a non-tertiary alcohol having between 4 and 14 carbon atoms, inclusive; 30 to 35 parts by weight of a hydrophilic, ethylenically unsaturated monomer; and 4 to 15 parts by weight of a polar, ethylenically unsaturated monomer different from the hydrophilic, ethylenically unsaturated monomer.

The second absorbent layer preferably functions as a pressure sensitive adhesive, and can control the rate of exudate influx into the first absorbent layer. In order for the second absorbent layer to function as an exudate rate-controlling membrane, the exudate absorbency of the second absorbent layer is typically lower than the exudate absorbency of the first absorbent layer. Preferably the exudate absorbency of the second absorbent layer is 2-fold lower than the exudate absorbency of the first absorbent layer. More preferably, the exudate absorbency of the second absorbent layer is 3-fold lower than the exudate absorbency of the absorbent layer.

The first and second absorbent layers combine to provide favorable absorbency and integrity. The first absorbent layer typically has the greatest capacity for absorbing exudate, but the second absorbent layer aids in providing integrity to the first absorbent layer. Such integrity is aided depending upon the implementation, by providing a physical barrier, an absorption rate control layer, and/or a physical strengthening layer. In a first regard, the second layer serves as a barrier because it is more durable than the first layer when fully saturated (in part because it is able to absorb less liquid). In a second regard, the lower absorbency of the second absorbent layer helps to regulate the rate of liquid uptake in the first layer. As such, the first layer can uniformly swell and show less disintegration. In a third regard, the second layer, particularly when it has adhesive properties, secures the portions of the dressing together, thereby adding strength.

The first absorbent layer is typically from 5 to 100 mils thick, and more typically from 10 to 50 mils thick. In specific preferred implementations, the first absorbent layer is 20 to 30 mils thick, and more preferably about 25 mils thick. The second absorbent layer is typically less than 50 mils thick, and more typically from 1 to 10 mils thick. In specific implementations, the second absorbent layer is from 2 to 4 mils thick, including implementations having a second absorbent layer that is 3 mils thick.

In most embodiments, the first absorbent layer is at least as thick as the second absorbent layer, and more typically significantly thicker than the second absorbent layer. Thus, the first layer can be up to 50 times thicker than the second layer in specific example embodiments. Generally, however, the thickness of the first layer is from 2 to 15 times the thickness of the second layer, and more typically from 5 to 10 times greater. In specific example embodiments, the first absorbent layer is about 8 times the thickness of the second absorbent layer.

One or more multifunctional crosslinking monomers may be included in the preparation of the absorbent layers. The term "multifunctional" as used herein refers to crosslinking monomers which have two or more free radically polymerizable, ethylenically unsaturated groups. Useful multi-functional crosslinking monomers include acrylic or methacrylic esters of diols, including 1,4-butanediol diacrylate, 1,4-butanediol dimethacrylate, neopentyl glycol diacrylate, 1,6-hexanediol diacrylate, 1,6-hexanediol dimethacrylate; acrylic or methacrylic esters of triols such as glycerol; and tetraols such as pentaerythritol.

Other useful multifunctional crosslinking monomers include polymeric multifunctional (meth) acrylates, e.g., alkylene glycol-type diacrylates or dimethacrylates, such as diethylene glycol diacrylate, diethylene glycol dimethacrylate, triethylene glycol diacrylate, diethylene glycol dimethacrylate, polyethylene glycol 200 diacrylate, polyethylene glycol 400 diacrylate, polyethylene glycol 600 diacrylate, polyethylene glycol 200 dimethacrylate, polyethylene glycol 400 dimethacrylate, polyethylene glycol 600 dimethacrylate, polyethylene glycol 1000 dimethacrylate, polypropylene glycol 400 diacrylate, polypropylene glycol 400 dimethacrylate; polyvinylic crosslinking agents such as substituted and unsubstituted divinylbenzene; trimethylolpropane-type tri- and tetra-acrylates or tri-methacrylates, such as trimethylolpropane triacrylate, trimethylolpropane trimethacrylate, ethoxylated trimethylolpropane triacrylate, trimethylolpropane tetraacrylate; pentaerythritol-type tri- and tetra-acrylates or tri- and tetra-methacrylates, such as pentaerythritol triacrylate, pentaerythritol tetramethacrylate; isocyanurate-type triacrylates or trimethacrylates, such as tris(acryloxyethyl) isocyanurate, tris(methacryloxyethyl) isocyanurate; and bisphenol A-type diacrylates or dimethacrylates, such as ethoxylated bisphenol A diacrylate, ethoxylated bisphenol A dimethacrylate; and difunctional urethane acrylates such as "EBECRYL" 270 and "EBECRYL" 230 (1500 weight average molecular weight and 5000 weight average molecular weight acrylated urethanes, respectively—both available from Radcure Specialties), and combinations thereof.

The polymerization reaction may be initiated using various methodologies, including photoinitiation, chemical initiation (such as using peroxide), and thermoinitiation. When photoinitiation is used, the amount of photoinitiator used in the monomer mixture differs according to the extinction coefficient thereof, but typically ranges from about 0.001 to about 5.0 parts by weight per 100 parts of total monomer, preferably from about 0.01 to about 5.0 parts by weight, and more preferably from about 0.05 to about 0.5 parts by weight.

Useful photoinitiators include acetophenone, 1-hydroxycyclohexyl phenyl ketone, 2-hydroxy-1-[4-(hydroxyethoxy)phenyl]-2-methyl-1-propanone, 2-hydroxy-2-methyl-1-phenylpropan-1-one, 1-(4-isopropylphenyl)-2-hydroxy-2-methylpropan-1-one, 1-(4-dodecylphenyl)-2-hydroxy-2-methylpropan-1-one, 4-(2-hydroxyethoxy)-phenyl-(2-hydroxy-2-propyl)ketone, 2-methyl-1-[4-(methylthio)phenyl]-2-morpholinopropane-1; substituted alpha-ketols such as 2-methyl-2-hydroxypropiophenone; benzoin photopolymerization initiators such as benzoin, benzoin methyl ether, benzoin ethyl ether, benzoin propyl ether, benzoin butyl ether, benzyl dimethyl ketal; benzophenone photopolymerization initiators such as benzophenone, benzoylbenzoic acid, methyl benzoylbenzoate, 4-phenylbenzophenone, hydroxybenzophenone, 4-benzoyl-4'-methyldiphenyl sulfide, 3,3,-dimethyl-4-methoxybenzophenone; and thioxanthone photopolymerization initiators such as thioxathone, 2-chlorothioxathone, 2-methylthioxathone, 2,4-dimethylthioxane, isopropylthioxathone, 2,4-dichlorothioxathone, 2,4-diethyloxathone, and 2,4-diisopropylthioxathone.

Other materials which may be added to the monomer mixture (before, during or after curing) include chain transfer agents or chain stopping agents for controlling molecular weight (e.g., carbon tetrabromide, mercaptans, alcohols, methacrylates, vinyl compounds such as alpha-methyl styrene, or other monomers), tackifiers, perfumes, deodorants, and antioxidants. Preferably, these other materials do not interfere with the polymerization or the function or clarity of the finished dressing.

The absorbent layers may also contain plasticizers. Specific examples of plasticizers suitable for use in the present invention are low molecular weight polyhydric alcohols such as ethylene glycol, diethylene glycol, triethylene glycol, propylene glycol, dipropylene glycol, glycerol, diglycerol, 2,3-butanediol, 1,2-butanediol, 3-methyl-1,3- butanediol, 3-methyl-1,3,5-pentanetriol, 2-ethyl-1,2-hexanediol, polyethylene glycol, methoxypolyethylene glycol, polypropylene glycol, polyoxyethylene butyl ether, polyoxyethylene, polyoxypropylene, polyoxypropylene glyceryl ether, polyoxypropylene sorbitol, and polyoxyethylene polyoxypropylene pentaerythritol ether each having an average molecular weight of 1,000 or less. The plasticizers are typically selected such that they do not significantly impair transparency.

The absorbent layers may be prepared by photoinitiated bulk polymerization according to the technique described in Martens et al., U.S. Pat. No. 4,181,752. For example, the polymerizable monomers and photoinitiator are mixed together in the absence of solvent and partially polymerized to a viscosity in the range from about 500 to about 50,000 centipoise to achieve a coatable syrup. The cross-linking agent (if needed) and any other ingredients are then added to the prepolymerized syrup. Alternatively, these ingredients (with the exception of the cross-linking agent) can be added directly to the monomer mixture prior to prepolymerization.

B. Backing Layer

A backing layer may be present in embodiments of the present invention. The backing layer is typically the layer farthest from the wound, and provides additional strength to the dressing. Preferably the backing layer is conformable to animal anatomical surfaces, and impermeable to liquid water.

The backing layer can be a transparent, conformable, elastomeric, moisture vapor permeable film. The backing film is preferably impermeable to liquid water and has a moisture vapor transmission rate (MVTR) of at least 300 g per 24 hr at 37° C. and 80% relative humidity. More preferably, the MVTR is at least 700 g per 24 hr at 37° C. and 80% relative humidity, and most preferable at least 2000 g per 24 hr at 37° C. and 80% relative humidity using the inverted cup method as described in U.S. Pat. No. 4,595,001. Preferably, the backing will allow some moisture to evaporate from the dressing while still maintaining a moist environment, will prevent the wound from drying out, and will prevent bacteria and viral ingress. It is also desirable that the backing be a low friction material, such as that disclosed in U.S. Pat. No. 5,643,187.

The dressing is preferably conformable to anatomical surfaces and stretches to accommodate flexion of joints and distension of skin. After the dressing stretches, ideally it has elastic properties so that the dressing returns to the same size as before stretching. The backing may have a thickness of from 15 to 100 micrometers, preferably 20 to 80 micrometers and more preferably 20 to 50 micrometers. The backing layer may further comprise a pressure sensitive adhesive layer to enhance adhesion to the first absorbent layer.

Various materials can be used as the backing material. Specific examples include papers, non-woven fabrics, natural fiber (e.g., cotton) fabrics, synthetic resin fabrics, synthetic resin films, synthetic resin foams, mesh-form or network papers, woven fabrics, and knit fabrics. Surgical tapes, medical pressure-sensitive adhesive sheets, pressure-sensitive adhesive dressings, constructed with the above films, foams, non-woven fabrics, woven fabrics, or knits can also be used as a backing material.

Examples of suitable backing materials include polyurethanes such as Estane polyurethanes (available for B.F. Goodrich, Cleveland, Ohio) including, for example, Estane 58237, Estane 58245, and Estane 58309. Other suitable backing materials include elastomeric polyester such as Hytrel polyester elastomer (E.I. duPont deNemours & Co., Wilmington, Del.), blends of polyurethane and polyester, and polyvinyl chloride. Thermoplastic polyether-amide block copolymers such as Pebax 2533 and Pebax 3533 (available from Atochem Co.); and polyether-ester block copolymers may also be used.

C. Wound-Facing Layer

The wound dressing of the present invention preferably comprises a porous or non-continuous wound-facing layer to provide a fluid permeable barrier between the wound site and the absorbent layers, but may be optionally non-porous or continuous. The wound-facing layer allows transport of moisture (i.e. fluid and vapor) from the wound to the absorbent layers and can help isolate the wound from other components of the dressing. The wound-facing layer is preferably soft, flexible, conformable, non-irritating and non-sensitizing. A variety of polymers may be used for the wound-facing layer, including polyurethane, polyethylene, polypropylene, polyamide or polyester materials. Further, the wound-facing layer may be in the form of moisture vapor permeable films, perforated films, woven-, non-woven or knit webs, or scrims. A preferred wound-facing layer comprises a polyurethane film.

In one useful embodiment, the wound-facing layer is conformable to animal (including human) anatomical surfaces, has a moisture vapor transmission rate of at least 300 grams per square meter per 24 hours at an 80% relative humidity differential at 40° C. (as described in Chen, U.S. Pat. No. 5,733,570), and contains perforations for passing wound exudate through the wound-facing layer. The wound-facing layer typically does not pass liquid water under normal wound treatment conditions except at the places in the wound-facing layer which are positively perforated to allow the exudate to pass into the absorbent layer. The preferred moisture vapor transmission rate of the wound-facing layer is at least 600 grams per square meter per 24 hours at an 80% relative humidity differential at 40° C.

The wound-facing layer may further comprise a pressure sensitive adhesive layer. The adhesive coated wound-facing layer should have the aforesaid MVTR. Porous or non-porous wound-facing layers such as perforated polyurethane, polyamide, polyester, polypropylene, polyethylene, polyether-amide, polyurethanes, chlorinated polyethylene, styrene/butadiene block copolymers ("Kraton" brand thermoplastic rubber, Shell Chemical Company, Houston, Tex.) and polyvinyl chloride and those described in U.S. Pat. No. 3,121,021 that are covered with a pressure sensitive adhesive that is not permeable to liquid water can be used for the wound-facing layer. Optionally these films can be perforated. Additional porous materials include woven, knit, and non-woven substrates. It is also desirable that the wound-facing layer be a low friction material, such as that disclosed in U.S. Pat. No. 5,643,187.

It is preferred that the wound-facing layer have the above mentioned moisture vapor or liquid permeability (1) so that maceration of the skin under the wound dressing does not occur or is minimized, (2) so that moisture build-up under the wound-facing layer does not cause the wound-facing layer and, therefore, the wound dressing to be lifted off the skin, and (3) to enhance proximation of the wound edges. Preferred wound-facing layers are thin polymeric films optionally coated with pressure sensitive adhesive which, in combination, have the above characteristics.

The diameter of perforations or apertures in the wound-facing film are preferably less than the thickness of the two absorbent layers. More preferably, the diameter is less than 70% of the thickness of the absorbent layers. And still more preferably, the diameter is less than 60% of the thickness of the absorbent layers.

The void area of the apertures is determined by measuring the average diameter of the apertures and then calculating the average aperture area. The number of apertures per unit area is also counted. Finally, the Percent Void Area is calculated by the equation:

Percent Void Area=[(average void area per aperture)*(number of apertures per unit area)*100]

It is preferable to use wound-facing film with a void area between 1 and 20%, more preferably between 3 and 10%, and most preferably between 4 and 8%. If the Percent Void Area is too low, the rate of fluid absorption will be slow. If the Percent Void Area is too high, the mechanical strength of the film will diminish to an unacceptable level.

D. Adhesive Layers

The wound-facing layer is normally attached to the wound site by means of an adhesive which can be continuous or non-continuous, such as pattern coated. Adhesives which can be used with the wound dressings of the invention include adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration -A-B-A- wherein each A is a thermoplastic polymer block with a glass transition temperature above room temperature (i.e., above about 20° C.) having an average molecular weight between about 5000 and 125,000, and B is a polymer block of a conjugated diene having an average molecular weight between about 15,000 and 250,000. Additional examples of useful adhesives are acrylic adhesives such as isooctyl acrylate/N-vinyl pyrrolidone copolymer adhesives and crosslinked acrylate adhesives such as for example those described in U.S. Pat. No. 4,112,213. Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310; a fibrous adhesive with low trauma properties as described in U.S. patent application Ser. No. 08/980,541, filed Dec. 1, 1997; or have especially good adhesion to wet skin, such as the adhesives described in U.S. patent application Ser. No. 09/329,514, filed Jun. 10, 1999; and PCT Publication Nos. WO 99/13866 and WO 99/13865.

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the absorbent layer, i.e. the adhesive may be coated non-continuously or at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are Polyslik S-8004, 83 pound (135.4 g/m$^2$) bleached silicone release paper supplied by H. P. Smith Co., Chicago, Ill., and 80 pound (130.5 g/m$^2$) bleached two-sided silicone coated paper (2-80-BKG-157) supplied by Daubert Chemical Co., Dixon, Ill.

A pressure sensitive layer may also be optionally included between the backing and the first absorbent layer and can be made from medical grade adhesives and methods that are publicly known. Preferred adhesives are acrylate copolymers described in U.S. Pat. No. RE 24,906, particularly a 97:3 iso-octyl acrylate:acrylamide copolymer. Also preferred is a 70:15:15 isooctyl acrylate: methoxypolyethyleneoxide acrylate:acrylic acid terpolymer as described in U.S. Pat. No. 4,737,410 (Example 31) and U.S. Pat. No. 5,849,325. Other useful adhesives are described in U.S. Pat. Nos. 3,389,827; 4,112,213; 4,310,509 and 4,323,557. If the backing extends beyond the area of the absorbent layers, the backing adhesive may also serve as a border skin contact adhesive.

The preferred embodiments for the facing and backing layers are thin conformable polymeric films. Generally the films are from 12 to 50 microns in thickness, preferably from 12 to 25 microns. Conformability is somewhat dependent on thickness, thus the thinner the film the more conformable the film.

E. Additional Materials

The wound dressing of the invention may also comprise a frame or film overlay that allows the dressing to be more easily applied to the wound. The frames are made of a relatively rigid material that maintains the shape of the dressing during handling and application to the wound site. Each frame is generally releasably adhered to the back surface of the backing film and is removed after application of the wound dressing. Suitable frames are described in U.S. Pat. Nos. 5,531,855 and 5,738,642 (Heinecke et al.).

The composition of this invention may also contain one or more pharmaceutically active agents. Examples thereof are antibacterial agents such as povidone iodine, iodine, silver, silver chloride, and chlorhexidine. Pharmaceutically active agents can be used alone or as mixtures thereof; further, medicaments can be added before the reaction product of this invention is cured as long as they do not interfere with polymerization or the function or clarity of the finished dressing. Pharmacologically active agents can also be added after the reaction product is cured as they do not interfere with the function or clarity of the finished dressing.

F. Arrangement of Layers

Many different constructions of absorbent dressings are possible with the wound-facing layer, the absorbent layers and the backing layer. In one embodiment, the areas of the wound-facing layer and the backing layer are greater than that of the absorbent layers, and the wound-facing layer is bonded to the backing layer, thereby forming a pouch, with the absorbent disposed between the two. The greater area of the facing or backing layer forms a periphery to which an adhesive layer and a release liner may be attached.

It is preferred that the wound-facing, absorbent and backing layers of the present invention be at least translucent and more preferably sufficiently transparent so that the wound site to which they are applied can be viewed through the dressing. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed.

It is preferred that the dressing be both transparent and colorless so that the color of the wound, exudate, and periwound skin may also be evaluated. Preferred transparent films for use as facing and backing layers that allow visual inspection of the wound site include polyurethane films, such as ESTANE™ polyurethanes (B.F. Goodrich, Cleveland, Ohio); elastomeric polyesters, such as HYTREL™ polyester elastomers (E. I. duPont deNemours & Co., Wilmington, Del.) and polyether block amides (PEBAX, Elf Altochem North America, Philadelphia, Pa.). Other useful films are those described in U.S. Pat. Nos. 4,499,896; 4,598,004; and 5,849,325 (Heinecke et al.).

G. Methods of Making and using Wound Dressings

The invention also features methods of treating an exuding wound that includes applying one of the above-described dressings to the wound and allowing the dressing to absorb body fluids exuded from the wound. Furthermore, the invention features transparent, elastomeric, body fluid-absorbing compositions that include the above-described reaction products and have the above-described properties.

In a further aspect, the invention features methods for preparing a transparent, elastomeric, body fluid-absorbing composition that includes exposing an essentially solvent-free mixture of monomers or pre-polymeric syrup to actinic radiation to form the composition. The mixture or syrup includes: (a) an acrylic or methacrylic acid ester of a non-tertiary alcohol having between 4 and 14 carbon atoms, inclusive; (b) a hydrophilic, ethylenically unsaturated monomer; and (c) a polar, ethylenically unsaturated monomer different from the hydrophilic, ethylenically unsaturated monomer. The resulting composition is essentially free of hydrocolloidal gel particles and capable of absorbing moderate to heavy amounts of body fluids while retaining its structural integrity and transparency. In preferred embodiments, the mixture or syrup further includes a photoinitiator and is exposed to ultraviolet radiation.

The absorbent layers of the wound dressing can be formed separately and then adhered together either with an adhesive composition or adhered using the inherent adhesive properties of the absorbent layers, or by incorporation of an additional adhesive between the two layers. In another implementation, the two layers are simultaneously cured together. Such simultaneous curing can be accomplished by forming layers of uncured monomer and then curing together. For example, the first layer of monomer can be deposited onto a surface, followed by deposit of the second layer of monomer, and concluded with curing of the two layers. Alternatively, the two layers of uncured monomer can be simultaneously deposited (such as by being coextruded) and then cured.

H. Examples

This invention is further illustrated by the following examples that are not intended to limit the scope of the invention. In the examples, all parts, ratios and percentages are by weight unless otherwise indicated. All materials are commercially available, for example from Aldrich Chemicals, unless otherwise indicated or described.

The following test protocols were followed in conducting the experiments:

Saline Absorbency Method

A dry wound dressing sample (5-cm square) was weighed ($W_o$) and placed in a 180-ml bottle containing 50 ml of 0.9% Sodium Chloride Irrigation (isotonic saline solution) USP (Baxter Health Care Corp., Deerfield Ill.) at room temperature. The bottle was capped and allowed to stand without agitation. The sample was removed at 24 hours, blotted dry, and weighed ($W_{24}$). The percent absorbency values were calculated using the following formula and the results reported as an average of three replications:

$$\text{Saline Absorbency } (\%) = (W_{24} - W_o) \times 100 / W_o$$

Calf Bovine Serum Absorbency Method

A dry wound dressing sample (10 cm×15 cm) was applied to the upper flange of a clear polycarbonate cup, similar to a Paddington cup as described in the British Pharmacopoeia, 1993, Addendum 1996, page 1943, HMSO London, England. The sample was positioned over the center of the cup cavity (3.8-cm diameter, 3-cm depth, 14-ml volume capacity) and the sample was held in place by its own pressure sensitive adhesive layer. The cup was then inverted and 12 g of calf bovine serum (Sigma-Aldrich Chemical Co.) was added to the cup through a port. The port was closed with a threaded plug and the cup was placed in an incubator at 40° C. and 20% RH. After 24, 48 and 72 hours the amount of unabsorbed serum was removed, weighed ($W_t$), and then added back into the cup. The cup plus sample was then returned to the incubator until the next sampling timepoint. The absorbency was calculated using the following formula and the results reported in grams as an average of three replications:

$$\text{Calf Bovine Serum Absorbency } (g) = 12 \, g - W_t$$

Peel Force Method

The peel force method was used to measure the force required to remove a wound-facing layer of an adhesive dressing sample from its core layer. A 2.54-cm wide double-coated adhesive tape (3M Brand Double Stick Tape, 3M Company, St. Paul, Minn.) was adhered to the full circumference of a rotatable metal wheel that was mounted on the lower jaw of an Instron machine (Model No. 1122; Instron Corp., Canton, Mass.). A 2.54-cm wide polyester silicone adhesive tape (No. 8402 tape, 3M Company) was adhered to the double-coated tape, adhesive side out. An adhesive dressing sample (2.54 cm×10.2 cm) was placed on the silicone tape with the core layer facing against the wheel and the wound-facing layer facing the operator. One end of the wound-facing layer was lifted away from the core layer to form a tab that was clamped onto the upper jaw of the Instron machine. The wound-facing layer was then peeled off of the core layer at a 90-degree angle and at a crosshead speed of 300 mm/min. The peel force was recorded in grams force per 2.54-cm width as an average of three replications.

Saline Extract Acidity Method

An adhesive dressing sample (5-cm square) was placed in a glass jar containing 50 ml of 0.9% sodium chloride solution. After 24 hours at room temperature, the pH of the solution was measured.

Example 1

Multi-Layer Absorbent Wound Dressing

A multi-layer absorbent wound dressing having a backing layer, a first absorbent layer, a second absorbent layer, and a wound-facing layer was prepared by the following procedure.

The first absorbent layer precursor composition (Composition A) was prepared as follows. Acrylic acid (528 g, BASF, Mt. Olive, N.J.), 50% (w/w) sodium hydroxide solution (99 g, J. T. Baker, Philipsburg, N.J.), and 2-hydroxy-1-[4-(hydroxyethoxy)phenyl]-2-methyl-1-propanone (1.32 g, Ciba Specialty Chemicals Corp., Tarrytown, N.Y.) were added to a glass jar and mixed until dissolved. Methoxypolyethyleneglycol 400 acrylate (2470 g, "NK Ester-AM-90G", Shin-Nakamura Chemical Co., Ltd., Japan) was added to the jar and mixed in by shaking the jar. Lauryl acrylate (198 g, Aldrich Chemical Co., Milwaukee, Wis.) and alphamethylstyrene (3.3 g, Aldrich)

were added and the entire composition was mixed by shaking the jar.

The second absorbent layer precursor composition (Composition B) was prepared as follows. Acrylic acid (239 g), 50 (w/w) sodium hydroxide solution (41.6 g), and 2-hydroxy-1-[4-(hydroxyethoxy)phenyl]-2-methyl-1-propanone (1.3 g) were added to a glass jar and mixed until dissolved. Methoxypolyethyleneglycol 400 acrylate (1016 g) was added to the jar and mixed in by shaking the jar. While stirring the resulting solution with a propeller, 2-ethylhexyl acrylate (1951 g, BASF Corp.) was added to provide the finished composition.

Compositions A and B were thickened separately to between 1000 and 2000 centipose by short exposure to UV light and an additional 3.25 g of 2-hydroxy-1-[4-(hydroxyethoxy)phenyl]-2-methyl-1-propanone was added and mixed into each composition. The thickened Composition B was knife-coated at a thickness of 3 mil (0.076 mm) onto a conventional polyester release liner, followed immediately by knife-coating of the thickened Composition A at a thickness of 25 mil (0.635 mm) onto the Composition B layer. A conventional polyester release liner was provided on top of the Composition A layer. The coated layers were then cured under UV lamps (350BL, Sylvania Corp., Danvers, Mass.) at a peak wavelength of 350 nm and an intensity of 7.3 mW/cm$^2$ and a dose of 2360 mJ/cm$^2$ through the top release liner to make the finished core laminate of the adhesive wound dressing. Additionally, the thickened Composition B was separately knife-coated at a thickness of 25 mil (0.635 mm) onto a conventional polyester release liner for later testing.

A wound-facing layer was prepared by perforating a TEGADERM™ dressing (3M Company) by ultrasonic means so that the dressing contained 40 holes/cm$^2$ with each hole having a diameter of approximately 15 mils (0.38 mm). The Percent Void Area was calculated to be 4.5%.

The release liner was removed from the Composition A layer (first absorbent layer) side of the core laminate and to this side was laminated by hand to the adhesive side of a TEGADERM™ dressing (backing layer). The release liner was then removed from the Composition B layer (second absorbent layer) side of the core laminate and to this side was laminated by hand to the non-adhesive side of the wound-facing layer. The resulting completed multi-layer absorbent wound dressing material was cut into 10-cm×15-cm samples for test evaluations. Samples were also subsequently packaged and sterilized by irradiating at approximately 30 kGy.

Example 2

Multi-Layer Absorbent Wound Dressing

A multi-layer absorbent wound dressing was prepared as described in Example 1, except that N-vinyl acetamide was substituted for the acrylic acid/sodium hydroxide components in the first absorbent layer precursor composition (Composition A) and this composition was prepared as follows.

N-Vinyl acetamide (600 g, Showa Denko, Japan), 2-hydroxy-1-[4-(hydroxyethoxy)phenyl]-2-methyl-1-propanone (1.2 g), and methoxypolyethyleneglycol 400 acrylate (2183 g) were added to a glass jar and mixed by shaking the jar until the N-vinyl acetamide was dissolved. Lauryl acrylate (210 g) and alpha-methylstyrene (3.0 g) were added and the entire composition was mixed by shaking the jar.

Also, the wound-facing layer in this example contained 40 holes/cm$^2$ with each hole having a diameter of approximately 20 mils (0.51 mm). The Percent Void Area was calculated to be 7.8%.

The resulting completed multi-layer absorbent wound dressing material was cut into 10-cm×15-cm samples for test evaluations.

Example 3

Multi-Layer Absorbent Wound Dressing

A multi-layer absorbent wound dressing was prepared as described in Example 1, except that the sodium hydroxide solution component was not added to either Composition A or Composition B. The resulting completed multi-layer absorbent wound dressing material was cut into 10-cm×15-cm samples for test evaluations.

Example 4

Multi-Layer Absorbent Wound Dressing

A multi-layer absorbent wound dressing was prepared as described in Example 1, except that the first absorbent layer precursor composition (Composition A) was prepared as follows. 2-Hydroxy-1-[4-(hydroxyethoxy)phenyl]-2-methyl-1-propanone (1.32 g) and methoxypolyethyleneglycol 400 acrylate (2995 g) were added to a glass jar and mixed by shaking the jar. Alpha-methylstyrene (3.3 g) was then added and the entire composition was mixed by shaking the jar. The resulting completed multi-layer absorbent wound dressing material was cut into 10-cm×15-cm samples for test evaluations.

Comparative Example 1

Absorbent Wound Dressing without Adhesive Barrier Layer

An absorbent wound dressing was prepared as described in Example 1, except that the second absorbent layer precursor composition (Composition B) was not prepared and the final wound dressing material did not contain a second absorbent layer. The resulting completed absorbent wound dressing material thus comprised a single first absorbent layer (Composition A layer) sandwiched between the backing layer and the wound-facing layer. This comparative wound dressing material was cut into 10-cm×15-cm samples for test evaluations.

Test Evaluations

Saline Absorbency Evaluation

Wound dressing samples from Examples 1, 2 and 4, a sample of the second absorbent layer from Example 1, and a commercial wound dressing sample (CLEAR-SITE™ dressing, available from ConMed Corp., Utica, N.Y.) were evaluated for saline absorbency according to the test method described herein. Observations were also noted of sample clarity when dry and when wet. The results are provided in Table 1 and show that the invention wound dressing samples (Examples 1, 2 and 4) had high absorbency (650–680%) of saline solution over a 24-hour period and had significantly higher absorbency than either the separate barrier layer (from Example 1) or the CLEAR-SITE™ wound dressing sample. All dressing samples in this test appeared clear when wet or dry.

TABLE 1

Saline Absorbency

| Example | Absorbency (%) | Clarity (Dry) | Clarity (Wet) |
|---|---|---|---|
| 1 | 660 | Clear | Clear |
| Second Absorbent Layer (from Ex. 1) | 90 | Clear | Clear |
| 2 | 650 | Clear | Clear |
| CLEAR-SITE ™ | 260 | Clear | Clear |
| 4 | 680 | Clear | Clear |

Calf Bovine Serum (CBS) Absorbency Evaluation

Wound dressing samples from Examples 1 and 4, Comparative Example 1 (CE-1), and four commercial wound dressing samples (CLEAR-SITE™ dressing; TEGAS-ORB™ dressing, available from 3M Company; COMFEEL™ dressing, available from Coloplast, Ltd., UK; and DUODERM™ dressing, available from ConvaTech, Montreal, Canada) were evaluated for calf bovine serum absorbency according to the test method described herein. Observations were also noted of sample residue that was present in the test cell. The results are provided in Table 2 and show that the invention wound dressing samples (Examples 1 and 4) had an increasing level of CBS absorbency between 24 and 72 hours, had a high level of absorbency (10 to 12 g) at 72 hours, and left no dressing sample residue in the test cell. In contrast, Comparative Example 1 (lacking a second absorbent layer) reached a maximum absorbency (12 g) before 24 hours and left sample residue in the test cell. Samples from Examples 1 and 4, and Comparative Example 1 showed significantly higher absorbency than the four commercial wound dressing samples.

TABLE 2

Calf Bovine Serum Absorbency

| Example | Absorbency (g) | | | Test Cell Residue |
|---|---|---|---|---|
| | 24 hours | 48 hours | 72 hours | |
| 1 | 8 | 11 | 12 | No |
| CE-1 | 12 | 12 | 12 | Yes |
| 4 | 7.7 | 9.5 | 10 | No |
| TEGASORB ™ | 5.2 | 7.1 | 8.5 | Yes |
| COMFEEL ™ | 3.9 | 5.5 | 5.5 | Yes |
| CLEARSITE ™ | 3.3 | * | — | No |
| DUODERM ™ | 2.2 | 3.4 | 3.8 | Yes |

*Lateral swell occurred between dressing sample and test cell; observed leaking of CBS.

Peel Force Evaluation

Wound dressing samples from Example 1 and Comparative Example 1 (CE-1) were evaluated for peel force (the force required to separate the wound-facing layer from the core layer) according to the test method described herein. The results are provided in Table 3 and show that a much greater force was required to separate the wound-facing layer from the absorbent core layer (having a second absorbent layer) of the invention wound dressing (Example 1) than from the core layer (not having a second absorbent layer) of the comparative wound dressing (Comparative Example 1).

TABLE 3

Peel Force

| Example | Peel Force (g/2.54 cm) | Standard Deviation |
|---|---|---|
| 1 | 303 | ±8 |
| CE-1 | 204 | ±3 |

Saline Extract Acidity Evaluation

Wound dressing samples from Examples 1–3 and Comparative Example 1 (CE-1) were evaluated for saline extract acidity according to the test method described herein. The results showed that wound dressing samples utilizing partially neutralized acrylic acid or N-vinyl acetamide in the first absorbent layer (Examples 1–2 and Comparative Example 1) had slightly acidic extract (pH=6.1, 5.8, and 6.0, respectively), whereas the wound dressing sample utilizing non-neutralized acrylic acid in the first absorbent layer (Example 3) had much more acidic extract (pH=3.2).

Various modifications and alterations of this invention will become apparent to those skilled in the art without departing from the scope and principles of this invention, and it should be understood that this invention is not to be unduly limited to the illustrative embodiments set forth hereinabove. All publications and patents are incorporated herein by reference to the same extent as if each individual publication or patent was specifically and individually indicated to be incorporated by reference.

What is claimed is:

1. A multi-layer wound dressing comprising:
    a first absorbent layer with an absorbency greater than 300 percent and containing the reaction product of a hydrophilic, ethylenically unsaturated monomer; and
    a second absorbent non-disintegrating layer in contact with the first absorbent layer and less absorbent of body fluids than the first absorbent layer;
    wherein the wound dressing is configured to be positioned on a patient's wound such that the second absorbent layer is between the first absorbent layer and the wound; and wherein the second absorbent aye is substantially insoluble in water.

2. The multi-layer wound dressing of claim 1, wherein the first absorbent layer comprises less than 10 percent by weight water prior to application to a patient.

3. The multi-layer wound dressing of claim 1, wherein the first absorbent layer is substantially insoluble in water.

4. The multi-layer wound dressing of claim 1, wherein the first absorbent layer comprises the reaction product of the hydrophilic, ethylenically unsaturated monomer; an acrylic acid ester of a non-tertiary alcohol having 4 to 14 carbon atoms; and a polar, ethylenically unsaturated monomer.

5. The multi-layer wound dressing of claim 4, wherein the non-tertiary alcohol has from 6 to 12 carbon atoms.

6. The multi-layer wound dressing of claim 4, wherein the first absorbent layer comprises the reaction product of about 30 to 100 parts by weight of the hydrophilic, ethylenically unsaturated monomer; about 0 to 30 parts by weight of the acrylic acid ester of a non-tertiary alcohol having from 4 to 14 carbon atoms; and about 0 to 40 parts by weight of the polar, ethylenically unsaturated monomer.

7. The multi-layer wound dressing of claim 4, wherein the first absorbent layer comprises the reaction product of about 50 to 80 parts by weight of the hydrophilic, ethylenically unsaturated monomer; about 5 to 30 parts by weight of the acrylic acid ester of a non-tertiary alcohol having from 4 to 14 carbon atoms; and about 10 to 30 parts by weight of the polar, ethylenically unsaturated monomer.

8. The multi-layer wound dressing of claim 4, wherein the polar, ethylenically unsaturated monomer comprises N-vinyl acetamide.

9. The multi-layer wound dressing of claim 4, wherein the polar, ethylenically unsaturated monomer comprises partially neutralized acrylic acid.

10. The multi-layer wound dressing of claim 1, wherein the second absorbent layer comprises the reaction product of an acrylic acid ester of a non-tertiary alcohol having from 4 to 14 carbon atoms; a hydrophilic, ethylenically unsaturated monomer; and a polar, ethylenically unsaturated monomer.

11. The multi-layer wound dressing of claim 10, wherein the second absorbent layer comprises the reaction product of about 45 to 80 parts by weight of the acrylic acid ester of a non-tertiary alcohol having from 4 to 14 carbon atoms; about 25 to 40 parts by weight of the hydrophilic, ethylenically unsaturated monomer; and about 2 to 20 parts by weight of the polar, ethylenically unsaturated monomer.

12. The multi-layer wound dressing of claim 1, wherein the first absorbent layer has an absorbency at least 100 percent greater than the absorbency of the second absorbent layer.

13. The multi-layer wound dressing of claim 1, wherein the second absorbent layer has an absorbency of at least about 50 percent.

14. The multi-layer wound dressing of claim 13, wherein the second absorbent layer has an absorbency of at least 80 percent.

15. The multi-layer wound dressing of claim 1, wherein the dressing is substantially transparent.

16. The multi-layer dressing of claim 1, wherein the dressing is curable.

17. The multi-layer wound dressing of claim 1, further comprising a wound-facing layer.

18. The multi-layer wound dressing of claim 17, wherein the wound-facing layer is perforated.

19. The multi-layer wound dressing of claim 1, wherein the second absorbent layer is adhesive.

20. A multi-layer wound dressing comprising:
a first absorbent layer having an absorbency of greater than 300 percent and containing less than 10 percent by weight water before application to a patient; and
a second absorbent layer having an absorbency of less than 50 percent of the absorbency of the first absorbent layer;
wherein the wound dressing is configured to be positioned on a patient such that the second absorbent layer is between the first absorbent layer and the wound; and
wherein the second absorbent layer is substantially insoluble in water.

21. The multi-layer wound dressing of claim 20, wherein the absorbency of the second absorbent layer is at least 50 percent.

22. The multi-layer wound dressing of claim 20, wherein the second absorbent layer is adhesive.

23. The multi-layer wound dressing of claim 20, wherein the wound dressing is transparent.

24. The multi-layer wound dressing of claim 20, wherein the first absorbent layer has an absorbency of at least 400 percent.

25. The multi-layer wound dressing of claim 20, further comprising an apertured wound-facing layer with a first side in contact with the second absorbent layer and a second side containing an apertured wound-facing adhesive layer.

26. The multi-layer wound dressing of claim 20, further comprising a backing.

27. The multi-layer wound dressing of claim 20, wherein the dressing is cutable.

28. The multi-layer wound dressing of claim 20, wherein the first absorbent layer is from 10 to 50 mils thick.

29. The multi-layer wound dressing of claim 20, wherein the second absorbent layer is from 2 to 4 mils thick.

30. The multi-layer wound dressing of claim 20, wherein the first absorbent layer is from 2 to 15 times as thick as the second absorbent layer.

31. The multi-layer wound dressing of claim 20, wherein the first absorbent layer comprises the reaction product of about 5 to 30 parts by weight of an acrylic acid ester of a non-tertiary alcohol having from 4 to 14 carbon atoms; about 50 to 80 parts by weight of a hydrophobic, ethylenically unsaturated monomer; and about 10 to 30 parts by weight of a polar, ethylenically unsaturated monomer.

32. The multi-layer wound dressing of claim 20, further comprising a wound-facing film having apertures having a total void area between 1 and 20 percent.

33. The multi-layer wound dressing of claim 32, wherein the wound-facing film has a void area between 4 and 10 percent.

34. The multi-layer wound dressing of claim 32, wherein the apertures have an average diameter less than the combined thickness of the first and second absorbent layers.

\* \* \* \* \*

UNITED STATES PATENT AND TRADEMARK OFFICE
CERTIFICATE OF CORRECTION

PATENT NO. : 6,903,243 B1
APPLICATION NO. : 09/657486
DATED : June 7, 2005
INVENTOR(S) : Scott A. Burton It is certified that error appears in the above-identified patent and that said Letters Patent is hereby corrected as shown below:

<u>Column 6</u>
Line 58, delete "N-acryloyloxyethyl)pyrrolidinone;" and insert in place thereof
-- N-(acryloyloxyethyl)pyrrolidinone; --.

<u>Column 18</u>
Line 40, delete "aye" and insert in place thereof -- layer --.
Line 64, delete "monomer," and insert in place thereof -- monomer; --.

<u>Column 19</u>
Line 32, delete "curable." and insert in place thereof -- cutable. --.

Signed and Sealed this

Twelfth Day of December, 2006

JON W. DUDAS
*Director of the United States Patent and Trademark Office*